(12) United States Patent
Laugharn, Jr. et al.

(10) Patent No.: US 9,274,028 B2
(45) Date of Patent: Mar. 1, 2016

(54) SAMPLE HOLDER WITH PLUNGER AND METHOD FOR EXPELLING SAMPLE

(71) Applicant: Covaris, Inc., Woburn, MA (US)

(72) Inventors: James A. Laugharn, Jr., Winchester, MA (US); Ion A. Tsinteris, Somerville, MA (US)

(73) Assignee: Covaris, Inc., Woburn, MA (US)

( * ) Notice: Subject to any disclaimer, the term of this patent is extended or adjusted under 35 U.S.C. 154(b) by 429 days.

(21) Appl. No.: 13/688,740

(22) Filed: Nov. 29, 2012

(65) Prior Publication Data

US 2013/0152710 A1 Jun. 20, 2013

Related U.S. Application Data

(60) Provisional application No. 61/566,181, filed on Dec. 2, 2011.

(51) Int. Cl.

| | |
|---|---|
| *G01N 1/08* | (2006.01) |
| *B01L 3/00* | (2006.01) |
| *A61B 10/00* | (2006.01) |
| *G01N 1/42* | (2006.01) |
| *G01N 1/28* | (2006.01) |

(52) U.S. Cl.
CPC .............. *G01N 1/08* (2013.01); *A61B 10/0096* (2013.01); *B01L 3/508* (2013.01); *B01L 3/5635* (2013.01); *G01N 1/42* (2013.01); *B01L 3/5082* (2013.01); *B01L 2200/0657* (2013.01); *B01L 2300/042* (2013.01); *B01L 2300/0851* (2013.01); *B01L 2400/0478* (2013.01); *G01N 2001/2866* (2013.01)

(58) Field of Classification Search
CPC .......... G01N 1/08; G01N 1/42; A61B 10/0283
See application file for complete search history.

(56) References Cited

U.S. PATENT DOCUMENTS

| | | |
|---|---|---|
| 4,989,678 A | 2/1991 | Thompson |
| 5,644,091 A | 7/1997 | Jacq et al. |
| 6,098,724 A | 8/2000 | Ricker |
| 6,712,161 B1 | 3/2004 | Dai |

FOREIGN PATENT DOCUMENTS

| | | | |
|---|---|---|---|
| DE | 10144127 C1 | 2/2003 | |
| WO | WO 95/31707 | 11/1995 | |
| WO | WO 2009/155430 A2 | 12/2009 | |
| WO | WO 2013082208 A2 * | 6/2013 | ............... G01N 1/08 |

OTHER PUBLICATIONS

International Preliminary Report on Patentability for PCT/US2012/066936, report issued Jun. 3, 2014.*
Invitation to Pay Additional Fees in PCT/US2012/066936, Mailed May 7, 2013.

* cited by examiner

*Primary Examiner* — Paul West
(74) *Attorney, Agent, or Firm* — Wolf, Greenfield & Sacks, P.C.

(57) ABSTRACT

Method and apparatus for holding and/or transferring a sample material into a second holder. The sample holder may comprise a shoulder arranged on the outer surface to engage a second holder and to position a top opening of the sample holder for communication with the second holder. A sample may be expelled from a sample holder using a piston that moves from a lower portion to an upper portion of the sample holder.

18 Claims, 6 Drawing Sheets

SAMPLE HOLDER WITH PLUNGER AND METHOD FOR EXPELLING SAMPLE

BACKGROUND

A first step in sample analysis typically involves collecting the sample. For example, a first step in a biological analysis such as RNA gene expression profiling or protein biomarker profiling is to collect a particular sample so that its biochemical constituents can be analyzed. After collection, the sample is typically stored, often in freezing conditions, before it is prepared for analysis. Often, to minimize perturbation of the biochemical profile of the sample, the tissue is flash-frozen (e.g., via direct immersion of the sample following procurement in liquid nitrogen) and stored at cryogenic temperatures (e.g., −80 degrees C. or lower), which inhibits degradative processes.

To prepare the sample for analysis, it is retrieved from storage and placed into a machine that fractures the sample into a plurality of smaller fragments to enable more accurate analysis. While fracturing, the samples are held in a special fracturing holder. Samples are typically stored in the same holder used for fracturing the sample. Using the same holder avoids complications associated with transferring a sample between two holders, such as contamination and failure to completely transfer the entire sample.

SUMMARY OF INVENTION

The inventors have appreciated, however, that storing a sample in a same holder used for fracturing may in some cases have disadvantages. For example, some fracturing holders are costly because they require special material that can withstand the fracturing forces and avoid rupturing during the fracturing phase. The cost of sample holders may be a concern because in many cases samples are collected and stored for future analysis, but are never actually analyzed. As a result, a relatively expensive sample holder intended for use in fragmenting a sample may be used for storage, but never employed for sample crushing. Also, some fracturing holders, such as a bag-like holder, may have an awkward size and/or shape and are thus inconvenient for storing large numbers of samples in an organized and compact arrangement. For example, because of their shape, some bags cannot be neatly stacked or otherwise organized in freezers, making storing and locating the samples difficult.

Aspects of the invention may address at least some of these challenges by providing, in various embodiments, devices and methods for collecting, storing, and/or transferring samples. As described above, analysis of biological and non-biological sample specimens often begins with collection of a sample. After collection, the sample is typically stored, often in freezing conditions, before being prepared for analysis (e.g., by fracturing the sample into smaller fragments). In one embodiment, a sample holder includes a vessel arranged so that a sample may be placed into the vessel, frozen (e.g., by exposure to liquid nitrogen or other suitable cryogen), stored (e.g., in the vapor phase of liquid nitrogen or in a mechanical freezer), and then transferred into a second holder (e.g., a fracturing holder) using a simple transfer technique without contaminating or wasting excess amounts of the specimen sample during the transfer.

A sample may include any material. Exemplary samples include, but are not limited to, bones, teeth, seeds, plants, pathological or non-pathological animal tissue (e.g., muscle, liver, kidney, lung, brain, pancreas, prostate, ovary, breast, etc.), tumor tissue, rocks, mineral samples, tree bark, and/or food products. Exemplary constituents include, but are not limited to, nucleic acids, amino acids, polypeptides, bacteria, viruses, fungi, spores, small organic molecules, small inorganic molecules, metals, minerals, ores, and the like. The sample may be relatively soft, such as a tissue sample, may be relatively hard, such as a bone or mineral sample, and may include sharp knife-like edges and/or sharp needle-like points. By way of a more particular example, a sample holder may be used to process pathological and/or non-pathological tissue samples harvested from a patient. Such samples include, but are not limited to, putative tumor samples taking during a biopsy.

In one aspect of the invention, a sample holder may include a vessel with a top with a top opening, a bottom with a bottom opening, and an interior space arranged to hold a sample. The interior space may be accessed through the top opening, e.g., for placement of a sample in the interior space. The holder may also include a stop in the interior space of the vessel, e.g., for interaction with a piston in the interior space. The piston may be disposed in the interior space and arranged to move from the stop at a lower portion of the interior space to an upper portion of the interior space to push a sample toward the top opening. The piston may be moved in the interior space by a pushing tool inserted into the bottom opening. The piston and the stop may be arranged to limit movement of the piston toward the bottom of the vessel. In some embodiments, the piston may be arranged to be removable from the vessel through the top opening, e.g., to aid in removal of the sample. In some embodiments, the interior space may have a same cross sectional area from a lower portion to an upper portion of the interior space, e.g., to allow the piston to move while maintaining a seal with the internal sidewall of the vessel. For example, the piston may have a piston cross sectional size that is approximately equal to the size of the top opening, e.g., so that the piston can be pushed through the top opening and out of the internal space. Such an arrangement may help facilitate removal of the sample from the holder. A cap may be arranged to sealingly engage with the top of the vessel to close the top opening. A shoulder may be provided on an outer surface of the vessel between the bottom and the top, e.g., for engaging with a second sample holder so as to position the sample holders in a desired way with respect to each other.

In another aspect of the invention, a method for transferring a sample from a first sample holder to a second sample holder includes associating a sample holder with the second holder so that a shoulder of the sample holder engages the second holder. The shoulder may position a top opening of the sample holder for communication with the second holder and resist the shoulder from entering internal space of second holder. The sample may be expelled from the top opening of the sample holder and into the second holder using a piston in the sample holder. For example, the piston may move from a bottom of the sample holder toward the top opening to push the sample from the interior space of the sample holder.

These and other aspects of the invention will be apparent from the following description and claims.

BRIEF DESCRIPTION OF DRAWINGS

Aspects of the invention are described with reference to illustrative embodiments shown in the drawings, in which like numbers reference like elements, and wherein.

DETAILED DESCRIPTION OF INVENTION

It should be understood that illustrative embodiments are described in accordance with aspects of the invention. However, the embodiments described are not necessarily intended to show or incorporate all aspects of the invention, but rather are used to describe a few illustrative embodiments. Thus, aspects discussed herein are not intended to be construed narrowly in view of the illustrative embodiments. In addition, it should be understood that aspects of the invention described may be used alone or in any suitable combination with other aspects also described.

Figure 1:
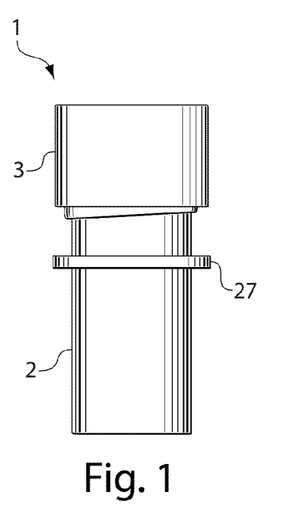
FIG. 1 shows a front view of a sample holder in an illustrative embodiment.
Figure 2:
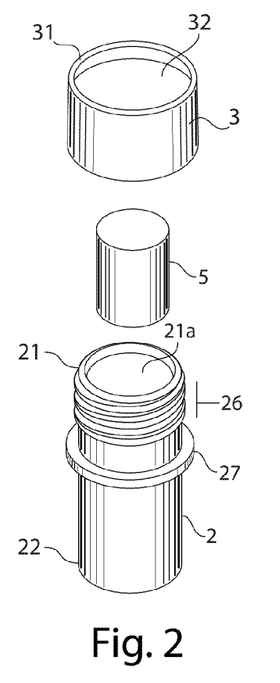
FIG. 2 shows an expanded top perspective view of the sample holder in FIG. 1.
Figure 3:
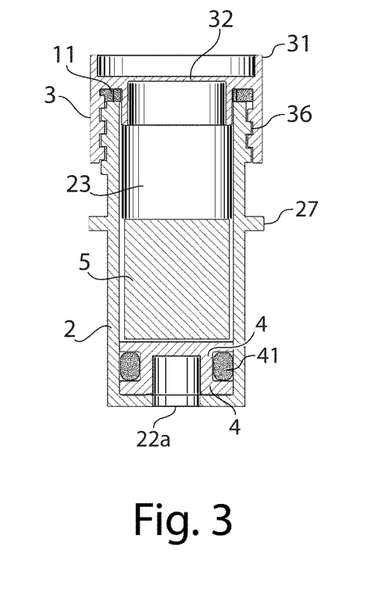
FIG. 3 shows a cross-sectional view of the FIG. 1 embodiment.

FIGS. 1 to 3 show an illustrative embodiment of a sample holder 1 that incorporates one or more aspects of the invention. In this embodiment, the sample holder 1 includes a vessel 2 that has a cylindrical shape, however, it should be understood that the vessel 2 may have any size, shape or other configuration, including cubic or box shapes, frustoconical shapes, other tubular shapes, etc. The vessel 2 includes a top 21 with a top opening 21a, a bottom 22 with a bottom opening 22a, and an interior space 23 arranged to hold a sample 5. The interior space 23 may have a same cross sectional area and/or shape from a lower portion to an upper portion of the interior space 23, but other arrangements are possible, such as one in which the cross sectional area increases or decreases from the lower portion to the upper portion. For example, the cross sectional area of the interior space at a lower portion may be slightly smaller than in upper portions of the interior space. This arrangement may help a piston 4 (discussed more below) engage the vessel sidewall when at the lower end of the interior space and form a seal. Alternately, or in addition, the cross sectional shape of the interior space 23 may change from the lower portion to the upper portion, e.g., from a square shape to a circular shape or others. According to this embodiment, the interior space 23 has a volume of about 700 μl and is arranged to hold a sample 5 of up to 500 mg, which may be introduced into the interior space 23 via the top opening 21a. It should be noted, however, that the interior space is not restricted to any particular volume and may be arranged for use with a wide variety of different samples and sizes. The holder 1 in this embodiment may be used to store a sample for any suitable length of time and in a variety of conditions based on the particular sample, its intended use, etc. Exemplary storage periods include short term storage for minutes (e.g., less than or equal to 30 minutes) or hours (e.g., less than or equal to 1 to 12 hours). Further exemplary storage periods include overnight storage or storage for 1 or more days, weeks, months, or years.

In accordance with one aspect of the invention, the sample holder 1 includes a cap 3 that is arranged to sealingly engage with the top of the vessel 2 to close the top opening 21a. The vessel 2 and cap 3 may be arranged for threaded engagement with each other by including threads 26 on an outer (or inner) surface of the vessel 2 and threads 36 on an inner (or outer) surface of the cap 3. A seal element 11, such as an o-ring, may be positioned between the top 21 of the vessel and the cap 3 to create a seal between the vessel 2 and the cap 3. However, other arrangements are possible, such as an interference or friction fit between the cap 3 and vessel 2 (where a portion of the cap fits inside the vessel or vice versa), a bayonet connection (as is found in some prescription medicine bottles), a flip top lid arrangement in which the cap 3 is mounted to the vessel 2 by a hinge, and so on. The cap may also include a recess 32 in a top portion 31 of the cap that matches the size and shape of the bottom 22 of the vessel so that the bottom 22 of the vessel can be received into the cap recess 32, e.g., to hold the cap 3 in place on the bottom 22 of the vessel 2. This arrangement may allow several sample holder 1 to be stacked one on top of each other for easy storing.

In accordance with another aspect of the invention, a piston 4 may be located within the interior space 23 and arranged to move in the interior space 23 from a lower portion to an upper portion, e.g., to expel a sample from the holder 1. Alternately, or in addition, the piston 4 may be arranged to be moved from an upper portion to a lower portion of the interior space 23 to draw a sample into the holder 1, e.g., by suction created by movement of the piston 4. The piston may include a seal element 41, such as an o-ring or other seal member, to create a seal between the piston 4 and the interior space 23. Alternately, a seal between the piston 4 and the vessel internal sidewall may be provided by a close fit of the piston to the vessel, a grease or other lubricant, a diaphragm or bellows that is fixed at one end to the piston and at another end to the vessel, and so on. Any sample 5 held in the interior space 23 may thus be sealed within the vessel 2 due to the cap 3 closing the top opening 21a and the piston 4 effectively closing off the bottom opening 22a. Alternately, a bottom 22 of the vessel may be closed by an additional cap or other element. A stop 24 may be provided at the lower portion of the interior space 23 to help prevent the piston 4 from moving beyond a desired point in the interior space 23. The stop 24 in this case includes a circumferential ridge within the interior space that protrudes from the inner surface of the vessel 2, but may have other arrangements, such as one or more protruding tabs, bumps or other features. In this embodiment, the stop 24 is located at the bottom opening 22a, but may be arranged above the bottom opening 22a, if desired.

In accordance with an aspect of the invention, the piston may have a piston cross sectional size and/or shape that is approximately equal to the size and/or shape of the top opening. This arrangement may allow the piston to be moved through the top opening 21a and out of the interior space 23 of the vessel, and aid in removal of a sample from the vessel. This arrangement is in contrast to some syringe-type configurations in which a piston is not removable from the vessel through the top opening.

In accordance with another aspect of the invention, the vessel 2 includes a shoulder 27 on the outer surface of the vessel 2 located between the bottom 22 and top 21 of the vessel. In this embodiment, the shoulder 27 includes a circumferential rim around the vessel and is located slightly closer to the top 21 than the bottom 22. However, other options are possible for a shoulder, such as a widening of the vessel 2 in a desired area (e.g., so that the bottom 22 has a larger circumference than the top 21), one or more portions of a screw thread (e.g., used to engage the cap 3) may provide a shoulder, one or more protrusions, tabs or other features extending from the vessel sidewall may provide a shoulder 27, and so on.

In accordance with another aspect of the invention, a sample holder 1 may be arranged to be used at cryogenic temperatures. To minimize perturbation of the biochemical profile of a tissue sample, to aid in fragmenting a sample by physical impact, or for other reasons, the a sample may be frozen (e.g., by dipping the sample holder 1 in liquid nitrogen) and then stored at cryogenic temperatures (e.g., about −40 degrees C. or lower). The sample holder 1 may be stored in the vapor phase of liquid nitrogen, in a mechanical freezer, or other conditions, until the sample 5 is prepared for analysis (e.g., by fracturing or other processes). In accordance with another aspect of the invention, the sample holder 1 may be arranged for barcode tracking so that the sample 5 may be easily stored, located, and retrieved for later analysis. For example, the vessel 2 and/or cap 3 may include a 2-dimensional barcode, RFID tag, alphanumeric text, or other machine readable identifier that can be read by a suitable reader and used to identify the holder 1 and/or sample, used to determine treatment processes for the sample, and so on.

Figure 4:
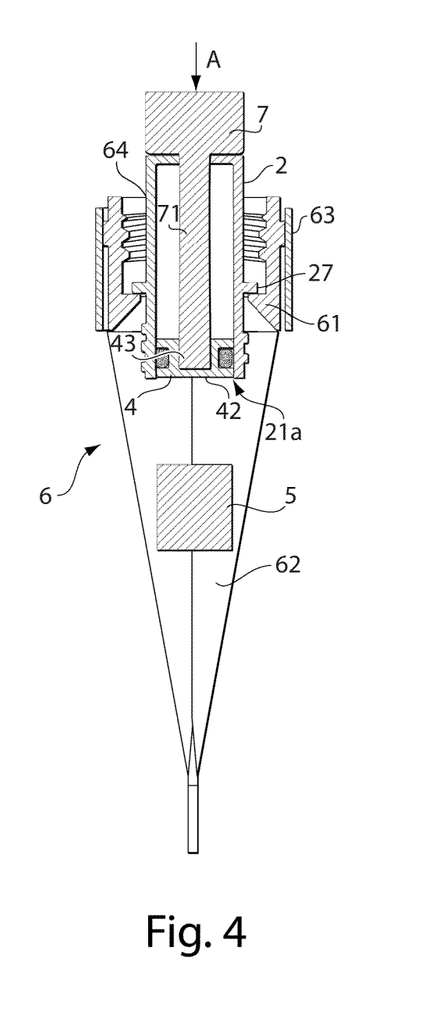
FIG. 4 shows a cross-sectional view of the holder in FIG. 1 in combination with a second holder.

In some embodiments, a sample holder 1 may be used to transfer a sample to another second holder, e.g., for sample fragmentation, acoustic energy treatment processes, etc., in a relatively simple way that helps avoid loss and/or contamination of the sample. FIG. 4 shows a cross-sectional view of the vessel 2 of the sample holder 1 engaged with a second holder 6 so that a sample 5 formerly held in the holder 1 is transferred to the second holder 6. To associate the sample holder 1 and second holder 6 for sample transfer, the holder 1 may be positioned with the top opening 21*a* facing upwardly and an opening of the second holder 6 placed over the top 21 so that the top 21 is received at least partially into the opening 64 of a port 63 of the second holder 6. (In this embodiment, the second holder 6 has a bag-like arrangement with a port 63 at a top end of the holder 6 that can be opened to receive a sample, such as that shown in US patent publication 2005/0132775. However, the second holder 6 may take other forms, such as a standard glass or plastic tube or vial, and need not necessarily have a port 63 as shown, be arranged for use in fragmenting a sample, or have other features of this illustrative embodiment.) The opening 64 in this arrangement is sized to accept the top 21 of the vessel, but is smaller than the shoulder 27 so that the holder 1 can be only partially passed through/into the port 63. Thus, the shoulder 27 of the sample holder 1 may be arranged to engage the second holder 6 to position the top opening 22*a* of the sample holder for communication with interior space 23 of the second holder 6, yet resist the shoulder 27 from entering internal space of the second holder 6 beyond a desired point. While the shoulder 27 may engage with a second holder 6 in different ways, according to this embodiment, the shoulder 27 engages a ridge portion 61 of the port 63 to position the top opening 21*a* within the interior space of the second holder 6, i.e., within the interior space of a bag portion 62 of the second holder 6. However, other positional arrangements are possible, such as positioning the top opening 21*a* in the port 63 and outside of the interior space of the second holder 6, or the shoulder 27 may be arranged so that the top opening 21*a* is positioned flush with an opening into the bag portion 62. The shoulder 27 may also, or alternately, help prevent the vessel 2 from being dropped into or otherwise entering the interior space of the second holder 6 in an undesired way.

To transfer the sample 5 to the second holder 6 and in accordance with another aspect of the invention, a pushing tool 7 may be used to move the piston 4 toward the top opening 21*a* and push the sample from the interior space 23. For example, the pushing tool 7 may have an elongated portion 71 that is inserted into the bottom opening 22*a* of the vessel and engaged with a bottom side 43 of the piston 4. In this embodiment, the bottom side 43 of the piston includes a recess matching the shape of the elongated portion 71 so that the elongated portion may be partially received into the piston 4, but this engagement is not required. When a force is exerted on the pushing tool 7 in a direction from the bottom 22 to the top 21 of the vessel, shown in FIG. 4 by arrow A, the elongated portion 71 of the pushing tool 7 extends into the vessel 2 and the piston 4 may be moved toward the upper portion of the interior space 23. When the piston moves from a bottom 22 of the sample holder 1 toward a top opening 21*a*, the sample 5 may be expelled through the top opening 21*a* of the sample holder 1 and into the bag portion 62 of the second holder 6. In one embodiment, the sample 5 may be at least partially solid, but may also take other forms (e.g., frozen, liquid or otherwise).

In accordance with an aspect of the invention, the pushing tool may be arranged to position the piston at a desired location in the vessel 2. For example, the elongated portion 71 may have a length so that when a handle end of the pushing tool 7 (or other stop feature of the tool 7) contacts the bottom 22 of the vessel 2, a top portion 42 of the piston is located at or near the top opening 21. This may help ensure that the sample 5 is fully expelled from the vessel 2 and/or expose the top portion 42 of the piston 4 to allow sample to be scraped or otherwise removed from the piston if necessary. Alternately, or additionally, the vessel 2 may include a stop at or near the top opening 21*a* or elsewhere in the vessel 2, to prevent movement of the piston 4 beyond a certain point. As discussed above, if the piston 4 forms a seal with the interior sidewall of the vessel 2 in the interior space 23, the entire sample 5 may be expelled into the second holder 6. However, even if the piston 4 does not form a seal with the vessel sidewall, all or most of the sample may be expelled by piston movement.

FIGS. 5 to 10 show another illustrative embodiment of a sample holder 1 that incorporates one or more aspects of the invention. In this embodiment, the stop 24 that resists piston movement toward the bottom 22 of the vessel 2 is located about midway between the top 21 and bottom 22 of the vessel 2. Although not required, the piston 4 includes a drive rod 44 that extends beyond the stop 24 toward the bottom 22 of the vessel. That is, while the piston 4 could be moved by a pushing tool 7 like that shown in FIG. 4, the extended drive rod 44 of the piston 4 in this embodiment allows for the use of a shorter pushing tool 7 than would otherwise be required.

Figure 5:
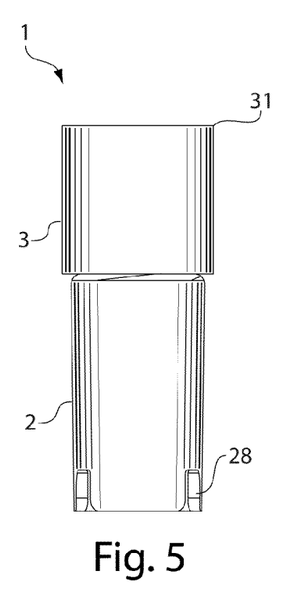
FIG. 5 shows a front view of a sample holder in a second illustrative embodiment.
Figure 6:
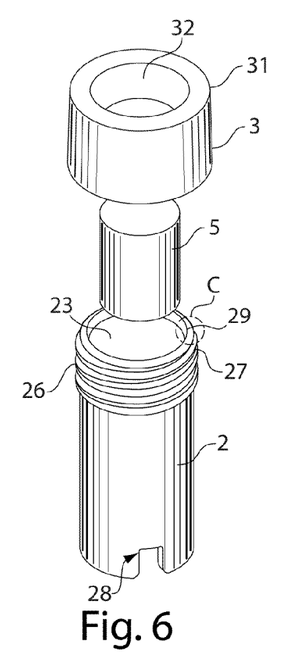
FIG. 6 shows an expanded top perspective view of the sample holder in FIG. 5.

In accordance with another aspect of the invention, the vessel 2 includes at least one anti-rotation feature, in this case a notch 28, in the bottom 22 of the vessel. The anti-rotation feature 28 may be a cutout in the bottom of the vessel wall that extends slightly toward the top as shown, and/or may be otherwise arranged, e.g., as a series of teeth, one or more depressions in the vessel outer sidewall, one or more protrusions, etc. The anti-rotation feature 28 may allow a user to engage the holder 1 in a tray or other location so as to provide for one-handed screwing and unscrewing of the cap 3. For example, the notch 28 may engage with a corresponding tab or other feature of a tray (or other component) that helps resist rotation of the vessel 2 relative to the tray. This may allow a user to remove and/or replace the cap 3 without being required to hold the vessel 2.

Figure 7:
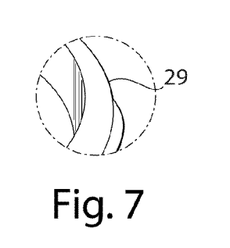
FIG. 7 shows an enlarged view of the portion identified by reference "C" in FIG. 6.
Figure 8:
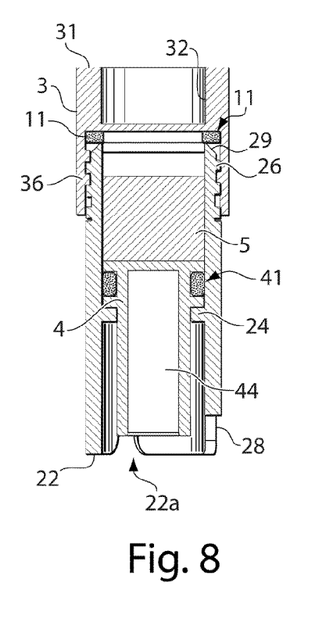
FIG. 8 shows a cross-sectional view of the FIG. 5 embodiment.

In accordance with another aspect of the invention, the top 21 of the vessel surrounding the top opening 22a may include a cutting tool 29, which may include a sharp edge, as shown in FIG. 7, a serrated blade or other feature. The cutting tool may allow a user to punch out or core a piece of tissue sample or other material, which can then be stored in the interior space 23 of the vessel 2. When taking such a sample, the piston 4 may be first moved toward the top opening 21a, and then withdrawn as the sample is taken so as to drawn the sample into the vessel 2. The piston 4 may be withdrawn by engaging a pushing tool 7 with the piston 4 (e.g., by interlocking the tool 7 with the piston 4 by way of a bayonet, friction fit or other suitable connection) and pulling the pushing tool 7 away from the top 21 of the vessel.

Figure 9:
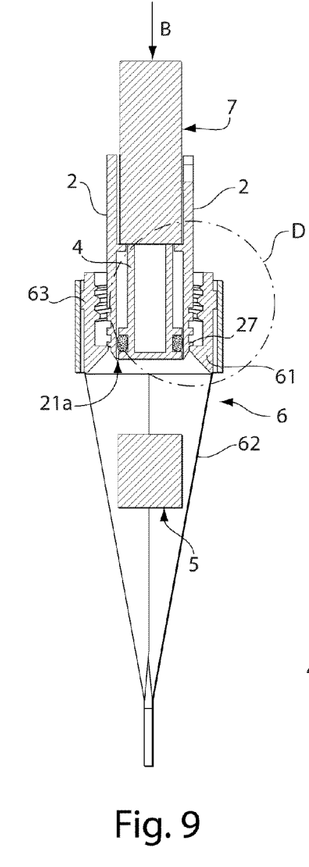
FIG. 9 shows a cross-sectional view of the holder in FIG. 5 in combination with a second holder.
Figure 10:
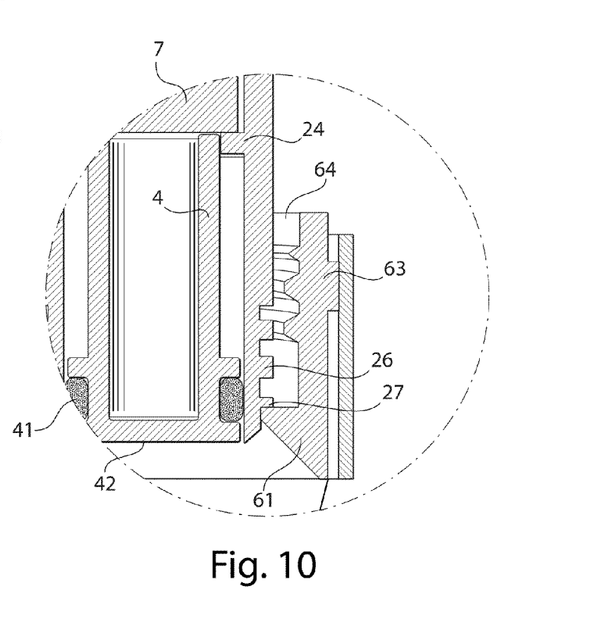
FIG. 10 shows an enlarged view of the portion identified by reference "D" in FIG. 9.

In accordance with another aspect of the invention, a portion of the threads 26 on the outer surface of the vessel 2 which engage with the cap 3 may provide a shoulder 27. FIGS. 9 and 10 show the holder 1 associated with a second holder 6 in a condition like that shown in FIG. 4. In this embodiment, the shoulder 27 (thread portion) engages a ridge portion 61 or other part of the second holder 6 to position the top opening 21a adjacent to the entrance to the bag portion 62 of the holder 6. Of course, engagement of the shoulder 27 with the second holder 6 may provide for any suitable positioning of the top opening 21a relative to the holder 6.

To expel the sample 5 from the vessel 2 and into the second holder 6, a pushing tool 7 (such as a simple rod-shaped element) may be inserted into the bottom opening 22a of the vessel 2 to engage the piston drive rod 44. When a force is exerted on the pushing tool 7 in a direction from the bottom to the top of the vessel, as indicated by arrow B, the piston 4 may be moved toward the top 21 of the vessel. The pushing tool 7 may extend into the vessel until it reaches the stop 24, which prevents the pushing tool 7 from extending further into the vessel 2. Thus, in this embodiment, the stop 24 may serve at least 2 functions: to prevent the piston 4 from moving beyond the stop 24 toward the bottom 22 of the vessel 2 and to prevent the pushing tool 7 from extending beyond the stop 24 toward the top 21 of the vessel 2. The piston drive rod 44 may have a length or otherwise be arranged so that when the pushing tool 7 is extended into the vessel to the stop 24, the piston 4 may move so that a top surface of the piston 42 is flush with, or otherwise suitably positioned with respect to, the top opening 21a. As described above, this may help ensure a complete discharge of the sample 5 from the sample holder 1 into the second holder 6. Of course, other arrangements are possible, as the piston 4 need not be positioned with a top surface 42 flush with the top opening 21a, but rather may be positioned above or below the top opening 21a, as desired. Also, or alternately, the vessel may be provided with a stop to control piston movement toward the top opening 21a, i.e., interaction of the pushing tool 7 with the stop 24 need not be used to define piston position.

Figure 11:
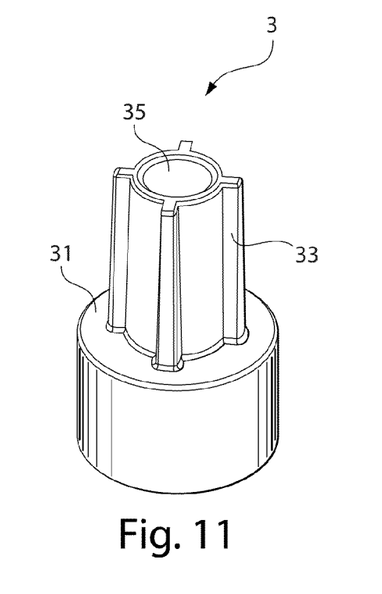
FIG. 11 shows a top perspective view of an illustrative embodiment of a cap.
Figure 12:
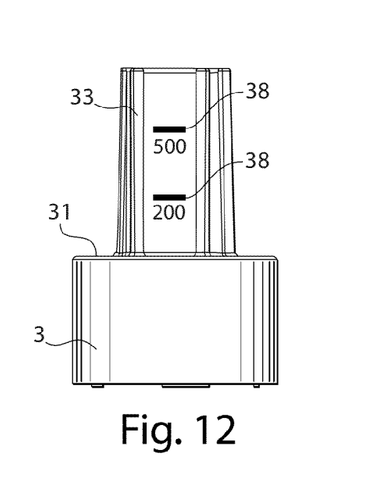
FIG. 12 shows a front view of the cap in FIG. 11.
Figure 13:
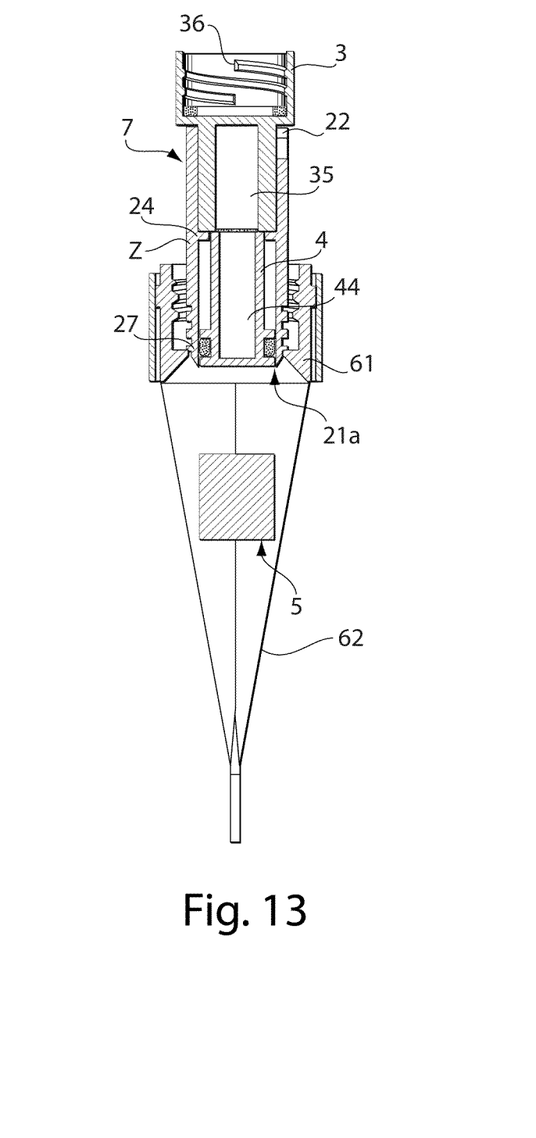
FIG. 13 shows a cross-sectional view of the cap in FIG. 11 used as a pushing tool to expel a sample into a second holder.

FIGS. 11 and 12 show another embodiment in which a portion of a cap 3 can function as a pushing tool 7. In this embodiment, the cap 3 has an extended portion 35 on a top surface 31 of the cap that provides a pushing tool 7. The extended portion 35 may be inserted into the bottom opening 22a of the vessel, as shown in FIG. 13, to move the piston toward the upper portion of the interior space 23. The extended portion 35 may have a length or otherwise be arranged so that when the top surface 31 of the cap (or other stop feature of the cap 3) contacts the bottom 22 of the vessel 2, a top portion 42 of the piston is located at or near the top opening 21. Also, or alternately, the extended portion 31 of the cap may have a length or otherwise be arranged so that when the extended portion 35 contacts a stop 24 in the vessel, a top portion 42 of the piston is located at or near the top opening 21.

In accordance with another aspect of the invention, the extended portion 35 may comprise one or more flanges 33 located on the extended portion 35. According to one embodiment, multiple flanges 33 extend longitudinally along the length of the extended portion 35 from the top surface 31 of the cap to a top of the extended portion. Alternately, the flanges may be otherwise arranged, e.g., partially longitudinally, circumferentially, one or more protrusions, tabs or other features extending from the extended portion 35. The one or more flanges 33 may provide a gripping surface that may facilitate screwing and unscrewing of the cap 3 to and from the vessel 2. Also, or alternately, the flanges may facilitate inserting the extended portion 35 into the bottom 22 of the vessel by providing guides to guide the extended portion 35 along an inner wall of the vessel 2 with reduced surface friction.

In accordance with an aspect of the invention, the pushing tool 7, vessel 2 and/or piston 4 may be arranged to provide for controlled movement of the piston 4, whether for sample discharge from the vessel 2 or sample collection. For example, as shown in FIG. 11, the pushing tool 7 portion of the cap 3 may include markings 38 that define different volume measures, such as 500 µL or 200 µL as shown. By aligning a respective marking 38 with the bottom 22 of the vessel 2, the pushing tool 7 part of the cap 3 may position the piston 4 in the interior space 4 so as to define the corresponding volume in the interior space 23. Thus, if the cap 3 is inserted into the bottom 22 of the vessel 2 so that the marking 38 for 500 µL is aligned with the bottom 22, a user can be assured that a volume of about 500 µL is defined by the piston 4 in the interior space. This feature may be useful when discharging a portion of a sample from the interior space 23, or when collecting a sample. For example, if it is known that a 700 µL sample is contained in the vessel 2, and a user wishes to discharge about 200 µL of the sample, the cap may be inserted into the bottom 22 of the vessel 2 so that the 500 µL marking 38 is aligned with the bottom 22 (meaning that 200 µL was displaced from the vessel). Similarly, if a user wishes to take a 500 µL sample and the interior space 23 has a 700 µL with the piston moved fully to the lower portion of the interior space 23, a user may insert the cap 3 so that the 500 µL marking 38 is aligned with the bottom 22 (meaning that the interior space 23 has a defined volume of 500 µL for the piston position and thus if the interior space 23 is filled with sample, a 500 µL volume will be collected). This arrangement may be useful when wishing to take a core sample of a defined volume. Of course, the markings 38 could be otherwise arranged, e.g., so that the markings 38 define a volume discharged from the vessel with the 500 µL being changed to 200 µL, and the 200 µL marking being changed to 500 µL from that shown in FIG. 11. Piston movement could also be more closely controlled to provide more accurate volume displacements, such as by having the pushing tool 7 engage with the vessel by way of a threaded connection. In this way, by screwing the pushing tool 7 into or out of the bottom 22 of the vessel, the piston 4 could be moved in a more controlled way in the interior space 23.

In another aspect of the invention, a method for transferring a sample includes associating a sample holder holding a sample with a second holder so that a shoulder on an exterior of the sample holder engages the second holder to position a top opening of the sample holder for communication with the second holder and resist the shoulder from entering internal space of second holder. The sample may be expelled through the top opening of the sample holder into the second holder by moving a piston in the sample holder from a bottom of the sample holder toward the top opening.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. It will be apparent that other embodiments and various modifications may be made to the present invention without departing from the scope thereof. The foregoing description of the invention is intended merely to be illustrative and not restrictive thereof. The scope of the present invention is defined by the appended claims and equivalents thereto.

The invention claimed is:

1. A sample holder comprising:
a vessel having a top with a top opening, a bottom with a bottom opening, an interior space arranged to hold a sample and accessible through the top opening, and a stop in the interior space;
a cap arranged to sealingly engage with the top of the vessel to close the top opening;
a piston disposed in the interior space and arranged to move from the stop at a lower portion of the interior space to an upper portion of the interior space to push a sample toward the top opening, the piston arranged to be moved in the interior space by a pushing tool inserted into the bottom opening, the piston and stop being arranged to limit movement of the piston toward the bottom of the vessel, the piston being arranged for removal from the interior space through the top opening; and
a shoulder on an outer surface of the vessel between the bottom and the top,
wherein a portion of the cap is arranged to function as the pushing tool.

2. The sample holder of claim 1, further comprising a push rod extending at a top surface of the cap to move the piston from the stop at the lower portion of the interior space to the upper portion of the interior space.

3. The sample holder of claim 1, wherein the vessel and the cap are arranged for threaded engagement with each other.

4. The sample holder of claim 1, further comprising a seal element to sealingly engage the cap and the top of the vessel.

5. The sample holder of claim 1, wherein the piston comprises a seal element to sealingly engage the piston with an interior sidewall of the vessel.

6. The sample holder of claim 1, wherein the top opening has a top opening size, and the piston has a piston cross sectional size that is approximately equal to the top opening size.

7. The sample holder of claim 1, wherein the interior space comprises a cylindrical interior space, the interior space having a same cross sectional area from the lower portion to the upper portion of the interior space.

8. The sample holder of claim 1, wherein the shoulder comprises a circumferential rim.

9. The sample holder of claim 1, further comprising a second holder comprising a port with an opening sized to accept the top of the vessel but smaller than the shoulder so that the holder can be only partially passed through/into the port opening.

10. The sample holder of claim 1, arranged for use at cryogenic conditions.

11. The sample holder of claim 1, wherein the interior space comprises a volume ranging up to approximately 700 µL.

12. The sample holder of claim 1, wherein the vessel is arranged to hold a sample having a mass up to 500 mg.

13. The sample holder of claim 1, wherein the piston comprises a drive rod extending below the stop.

14. The sample holder of claim 1, wherein the cap comprises an extended portion with longitudinally extending protrusions.

15. The sample holder of claim 1, wherein the cap comprises a recess that is arranged to receive the bottom of the vessel.

16. The sample holder of claim 1, wherein the vessel further comprises at least one or more anti-rotation features in the bottom.

17. The sample holder of claim 1, wherein the top comprises a cutting tool.

18. The sample holder of claim 1, wherein the shoulder comprises a thread on an outer surface of the vessel.

* * * * *